(12) United States Patent
Howard et al.

(10) Patent No.: US 7,806,964 B2
(45) Date of Patent: Oct. 5, 2010

(54) SYSTEM AND METHOD EXTRACTING COMPRESSION HEAT IN BIO-GAS TREATMENT PLANT

(76) Inventors: Lowell E. Howard, 11206-167th Ct. NE., Redmond, WA (US) 98052; Jeffrey V. Wetzel, 10532 Vernon Rd., Lake Stevens, WA (US) 98258

( * ) Notice: Subject to any disclaimer, the term of this patent is extended or adjusted under 35 U.S.C. 154(b) by 279 days.

(21) Appl. No.: 12/215,633

(22) Filed: Jun. 27, 2008

(65) Prior Publication Data
US 2009/0000482 A1    Jan. 1, 2009

Related U.S. Application Data

(60) Provisional application No. 60/937,587, filed on Jun. 27, 2007.

(51) Int. Cl.
*B01D 53/04* (2006.01)
(52) U.S. Cl. ............... 95/115; 95/141; 95/148; 96/146
(58) Field of Classification Search ............ 95/114, 95/115, 141, 148; 96/143, 144, 146
See application file for complete search history.

(56) References Cited
U.S. PATENT DOCUMENTS

| | | | | |
|---|---|---|---|---|
| 4,000,990 A | * | 1/1977 | Bingham | 95/103 |
| 4,770,676 A | * | 9/1988 | Sircar et al. | 95/99 |
| 4,784,672 A | * | 11/1988 | Sircar | 95/97 |
| 5,059,405 A | * | 10/1991 | Watson et al. | 423/210 |
| 5,451,249 A | * | 9/1995 | Spiegel et al. | 95/117 |
| 5,846,295 A | * | 12/1998 | Kalbassi et al. | 95/105 |
| 5,938,819 A | * | 8/1999 | Seery | 95/104 |
| 6,221,130 B1 | * | 4/2001 | Kolodziej et al. | 95/41 |
| 6,984,258 B2 | * | 1/2006 | Niclout et al. | 95/115 |
| 2008/0257158 A1 | * | 10/2008 | Howard | 96/127 |

* cited by examiner

*Primary Examiner*—Frank M Lawrence
(74) *Attorney, Agent, or Firm*—Dean A. Craine

(57) ABSTRACT

The system and method for recycling the compress heat generated at a bio-gas treatment plant that includes the assembly of a heat exchanger at each stage of compression designed to utilizing all of the gas flow and to harvest the heat in gas delivered to the air exchangers. After the heat is harvested, it is then conveyed either as hot air, or as a hot liquid, to a jacketed vessel containing media that requires regeneration or stripping of harmful VOCs picked up during the purification of contaminated landfill or municipal digester gas. The harvesting and conveyance of the heat of compression of the gases to a jacket around the vessel interior (indirect contact) and simultaneously heating the vessel interior containing the spent media through hot gas from another source (direct contact), reduces the heat-up time. This also reduces the overall the cycle time between the contaminant pick-up step and contaminant stripping step in regenerable treatment systems.

17 Claims, 2 Drawing Sheets

SYSTEM AND METHOD EXTRACTING COMPRESSION HEAT IN BIO-GAS TREATMENT PLANT

This is a utility patent application which claims benefit of U.S. Provisional Application No. 60/937,587 filed on Jun. 27, 2007.

BACKGROUND OF THE INVENTION

1. Field of the Invention

This invention pertains to heat recycling systems, and more particularly to heat recycling systems used in bio-gas treatment plants.

2. Description of the Related Art

It is well know that the compression of gases produce heat. In systems that generate a large amount of compressed gas, the amount of heat produced is substantial.

In a landfill or sewage treatment plant, low pressure fuel gases are produced that must be compressed for use with gas fired turbine generators. Typically, the heat produced by compressing the gas is partially collected by open heat exchangers. Unfortunately, a large portion of the heat is wasted and released into the atmosphere.

The invention disclosed herein pertains to systems used to more efficiently capture the wasted heat and recycle it into bio-gas treatment systems.

SUMMARY OF THE INVENTION

It is an object of the present invention to provide system for cleaning and harvesting contaminated bio-gas.

It is another object of the present invention to provide such a system where the heat of compression of the bio-gas is harvested and used to remove contaminants from the bio-gas. t.

It is another object of the present invention to provide such as system enables the operator to easily switch between decontamination and scrubbing modes.

These and other objects are met by the method and system for use of compression heat generated in a bio-gas treatment plant disclosed herein that includes a heat exchanger located at each stage of compression designed to harvest the heat produced when compressing the cleaned bio-gas and then use the harvested heat to heat the outer jacket of absorber used to scrub contaminates from the bio-gas.

After the heat is harvested, it can be conveyed either as a hot air or a hot liquid, to an outer jacket. By harvesting and conveyance of the heat of compression of the bio-gas to the jacket (indirect contact) and simultaneously heating the vessel's interior containing the spent media using a heated inert gas (direct contact), the overall time for heating the vessel is reduced. This also reduces the overall cycle time between the contaminant pick-up step and contaminant stripping step.

The system uses at least one adsorber with at least one jacket that is filled with hot air created by one or more gas compressors used to pressurize the bio-gas. The jacket surrounds a canister filled with activated carbon, silica gel, porous graphite, natural and synthetic zeolites, and molecular sieves or combinations of these is a specially designed contactor vessel to facilitate the use of the recovered heat. If more heat is needed to raise the temperature of the absorber, an inert gas generator is used to create another heated gas that is delivered to the jacket. The system is partially self-generating in that the cleaned bio-gas created may be used as a fuel for burning the contaminants and in the inert gas generator.

DESCRIPTION OF THE PREFERRED EMBODIMENT(S)

A system 10 for capturing and conveying the heat from gas compressors to aid or drive the removal of moisture and VOC/organosilicon compounds from bio-gas. The system 10 transmits the heated fluids from a plurality of compressor(s) used at different stages to pressurize the gas. Heat from the compressors is then used to provide uniform and constant temperature control.

Figure 1:
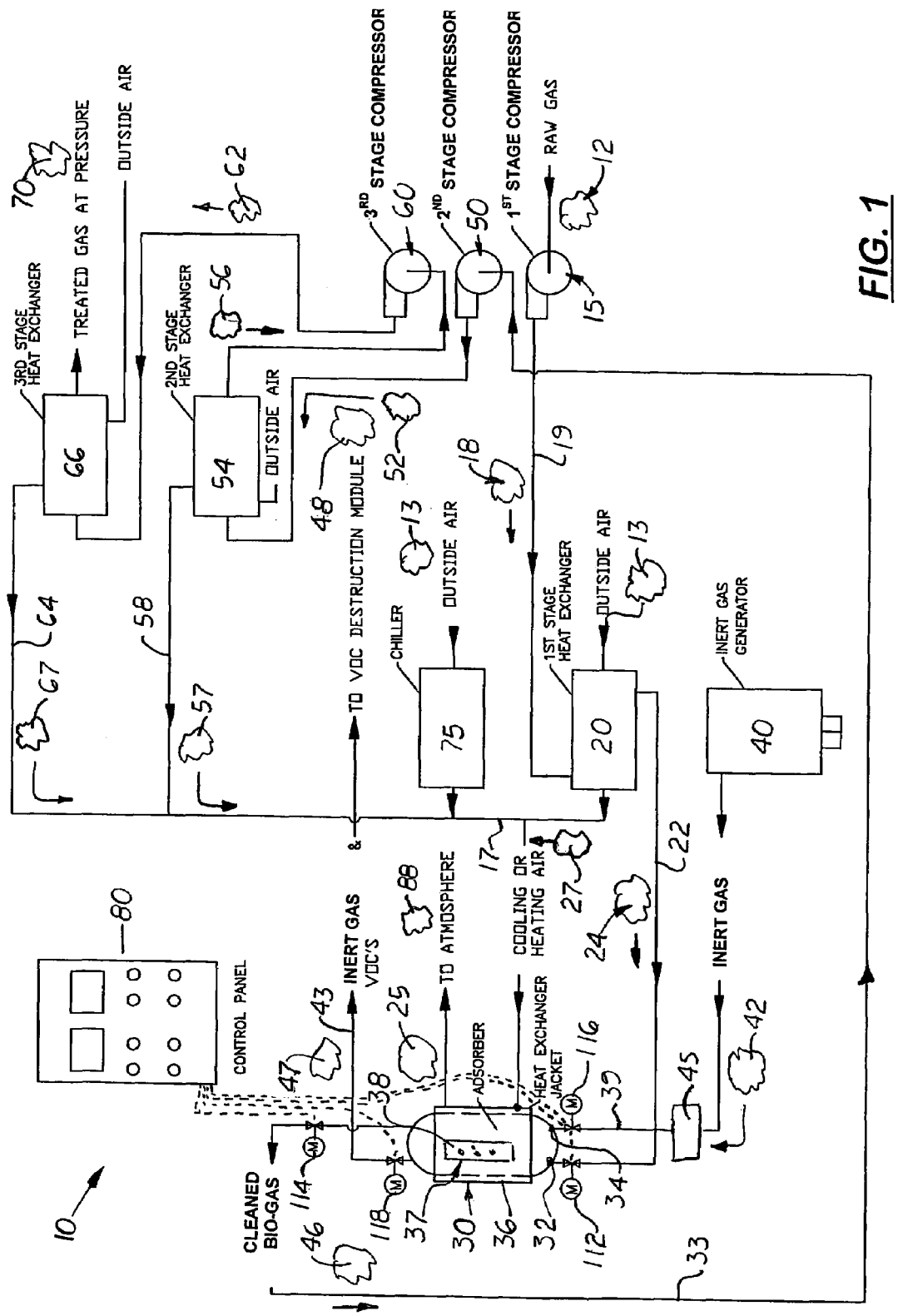
FIG. 1 is a diagram of the system for capturing and conveying the heat from gas compressors to aid or drive moisture and VOC/organosilicon compound removal from biogas.

As shown in FIG. 1, raw bio-gas 12 is received by the first stage compressor 15. This bio-gas 12 is produced by the landfill or waste water treatment plant digester, or some other source of methane, and typically has the moisture removed from the gas prior to the compression. The bio-gas 12 is compressed by the first stage compressor 15 to a pressure of approximately 100 psi. The hot, compressed bio-gas, now designated 18, is then delivered via a first conduit 19 to a first stage heat exchanger 20 and cooled. The raw gas, now designated 24, is cooled by the first stage heat exchanger 20 and is then delivered to an adsorber 30 via a first cooled gas conduit 22. Cooled outside atmospheric air 13 which is uses as a cooling media, is delivered to the first stage heat exchanger 20 which is heated and then delivered to a heat air conduit line 17 that connects to a heat jacket 36 located on an adsorber 30.

The adsorber 30 includes a cooled gas input port 32 which connects to the first cool gas conduit 22 that connects to the first stage heat exchanger 20. The cooled raw gas 24 travels upward in the adsorber 30 through a carbon media 38 located inside a removable canister 37 located inside the adsorber 30. After traveling through the canister 37, the cooled, cleaned bio raw gas, now designated 46, then exits the top of the adsorber 30 and travels via a first output conduit 33 to a second stage compressor 50. During the stage in the process, no heat is delivered to the adsorber 30.

In order to recover the carbon media 38, heat must be delivered to the adsorber 30. In the preferred embodiment, the adsorber 30 includes an inert gas input port 34 which connects to an input inert gas conduit 39 that connects to an inert gas generator 40. The inert gas generator 40 produces a heated inert gas 42, such as carbon dioxide, which is released into the adsorber 30 and used as a heat source to remove the contaminates from the carbon media 38. In the preferred embodiment, the inert gas 42 is heated to approximately 600 degrees. The inert gas 42 and the contaminants are then transferred from the adsorber 30 via a third conduit 43 to a burner or similar destruction module 48. In the preferred embodiment, the oxygen concentration of the inert gas 42 should be relatively low to eliminate explosions. An optional blower 45 may be provided to forcibly delivers the heated inert gas 42 to the adsorber 30.

In addition to stripping the raw bio-gas 24 of contaminants, the absorber 30 is also used as a media recovery vessel. In the preferred embodiment, the adsorber 30 has an outer heat exchange jacket 36 which returns the heated air 27, 57, 67 from the heat exchangers 20, 54, 66, respectively. In the preferred embodiment, the heated air 27, 57, 67 is mixed with the inert gas 42 and remains inside the outer jacket 36 to indirectly heat the carbon media.

Referring again to FIG. 1, the cooled, cleaned bio-gas 46 from the adsorber 30 is delivered to a second stage compressor 50 which compresses the bio-gas 46 to approximately 150 to 200 PSI. From the second stage compressor 50, the compressed cleaned bio-gas, now designated 52, is then delivered to a second stage heat exchanger 54 where excess heat is again removed. The cooled cleaned bio-gas 56 from the second stage heat exchanger 54 is then delivered to a third stage compressor 60 where it is pressurized to 250 to 300 PSI. A heat conduit 58 is used to deliver the heat from the second heat exchanger 54 to the heat exchanger jacket 34. The compressed cleaned bio-gas from the third stage compressor 60 is then delivered to the third stage heat exchanger 66 where excess heat is again removed. A heat conduit 64 is used to deliver the heat from the third heat exchanger 54 to the heat exchanger jacket 36. The cooled bio-gas, now designated 70, is then released from the third stage heat exchanger 66 at pressure and delivered to a collection tank or vessel (not shown).

During operation of the system 10, the adsorber 30 must be taken out of service to recycle the carbon media. During the recycle process, hot inert gas 42 generated in the inert gas generator 40 is delivered to the adsorber 30 and directly contacts the media. In this system 10, heat recovered from the first, second, and third heat exchangers 20, 54, 66, respectively, is sent through the external jacket 36 on the adsorber 30 to expedite the heating process.

During the media recovery cycle, the adsorber 30 and the jacket 36 are hot and must be rapidly cooled so that contaminated bio-gas can be cleaned by the carbon media. In the preferred embodiment, a chiller 75 is provided that collects cool outside air 13 and delivers it to the outer jacket 36 on the adsorber 30.

The system includes a plurality of valves 112, 114, 116, 118 that connect to the conduits 22, 133, 39, and 43, respectively, to the absorber 30 to the first heat exchanger 20, the first stage compressor 50, the inert gas generator 40, and the VOC Destruction module 48, respectively. The valves 112-118 connect to a control panel 80. During operation, the valves 112-118 are opened and closed by a control panel 80, so that during one stage the bio-gas flows continuously in the system 10 and cleaned and during a second stage, the carbon media 38 inside the adsorber 30 is scrubbed using the inert gas from the inert gas generator and the heated air from the three heat exchangers.

In the embodiment shown in the accompanying FIG. 1, only one absorber 20 is used. It should be understood however, that the system 10 can be used with multiple absorbers. For example, a second adsorber (not shown) could be provided that processes the bio-gas 18 from the first stage of compressor 15 until it reaches it's timed out period. The control panel 80 switches between the two absobers so that a continuous supply of pressurized bio-gas is produced.

Figure 2:
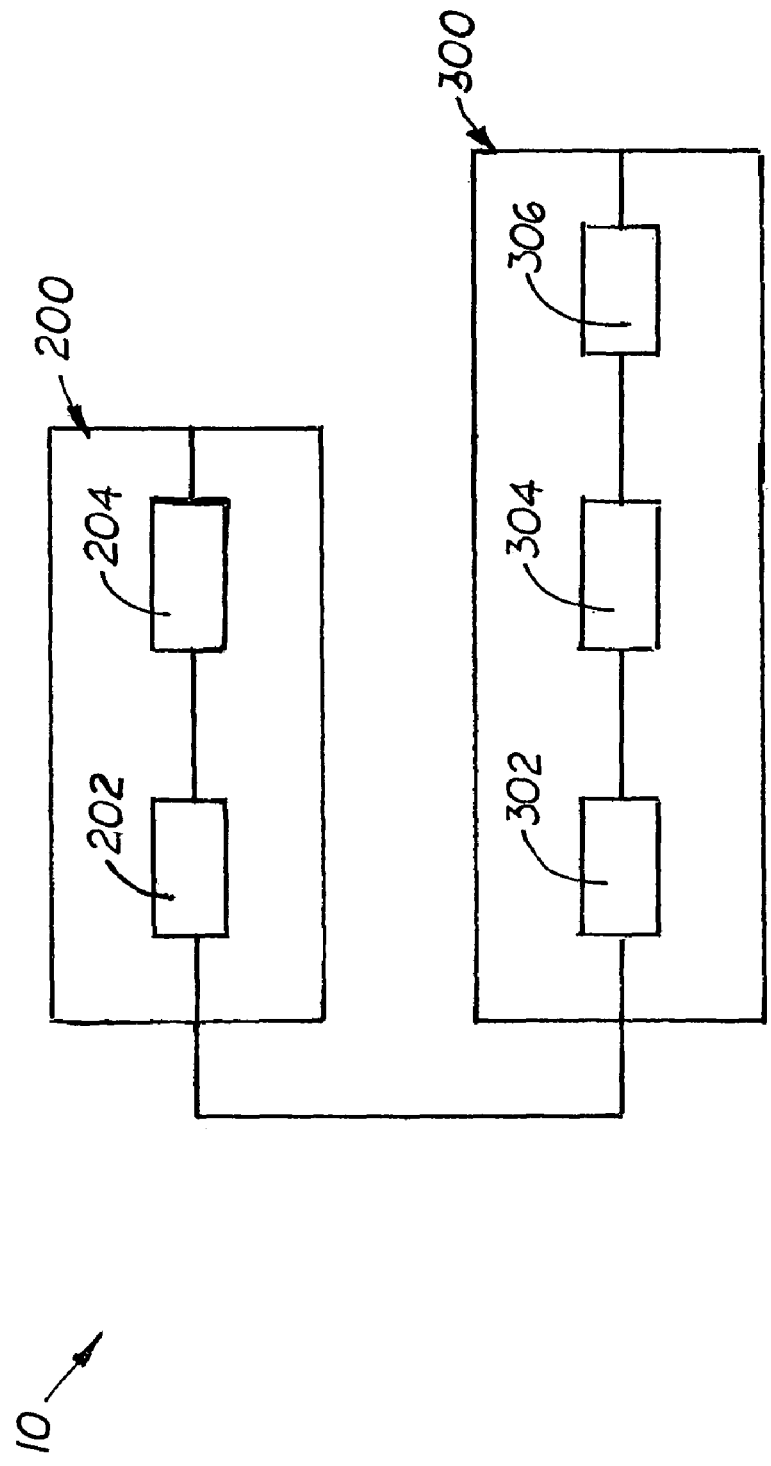
FIG. 2 is an illustration showing the system with a plurality of adsorbers aligned in a series.

As shown in FIG. 2, the system 10 could include several trains 200, 300 with two or three adsorbers 202, 204, and 302, 304, 306, aligned in a series in each train. In such a system, when the gas contamination reaches a specific level, more than one adsorber may be used in a train. If the contaminates are at a high level, a train cannot last for more than, say 7 hours before its carbon media needs to be regenerated. In this instance, several trains would be necessary. The first train goes until its carbon media is spent. The second adsorber is then placed on line while the first adsorber is regenerated. The third adsorber is the next in line, and will be operating while the second is being regenerated, and first train is being cooled and in standby mode.

Preliminary calculations show that the use of this recovered compressor heat can reduce the amount of energy that would otherwise have to be spent by heating air or inert gases through electrical coils or by burning part of the purified gas stream to generate hot, inert gas, by between 15% and 40%, depending on how the system is configured. Further, the use of this excess heat would also reduce the heat-up time, thereby decreasing the time interval between purification campaigns. Further, because the cycle times between purification campaigns can be reduced, the size of the equipment can also be reduced, saving on both capital and O&M costs of the treatment equipment.

The above described system was originally conceived to utilize heat from the compression of low BTU fuel gases, such as landfill gas and municipal anaerobic digester gas to the pressure required by large gas-fired turbine generators for such fuels. Typically, this heat of compression is rejected to the atmosphere by the use of open heat exchangers, similar to the radiators in automobiles. In this case, typically the hot gas passes through finned tubes and is cooled by a large fan blowing air across them. Normally, one stage of compression will elevate the pressure of a gas from a fraction of a psig and around 100 degrees F. to approximately 125 psig and a temperature over 350 degrees F.

Compressing the gas beyond this pressure in a single stage produces diminishing returns from an efficiency and cost perspective. The gas must be cooled back to nominally 90 degrees F. before it can be compressed again in subsequent stages. Large power generation turbines require low BTU (nominal 50% methane) gas to be compressed to 250 psig or 350 psig with each stage of compression boosting the gas approximately 125 psig.

Due to on-board heat rejection equipment and losses through natural convection, the gas from each stage of compression is nominally around 200 degrees F. It is the heat in the gas at this temperature that is harvested and used in the gas purification process.

Of particular interest to the inventor are treatment systems for the removal of organosilicons in the form of siloxanes, silanes, silanols, halosilanes, and halosilanols. These contaminants are virtually ubiquitous in biogas, originating from various personal care products and industrial chemicals. These organosilicons impart silicon dioxide and silicates upon combustion of fuel gases containing them. The damage from the organosilicons can cause expensive damage to power generation equipment or even cause its total failure.

A recent development in the area of biogas treatment equipment is the use of systems that contain media and are regenerable by the use of either hot air or hot gases. The use of energy in these systems robs this energy from the power generation process. In addition, gas conditioning systems are most often required that also rob energy that could be sold for a profit. This invention enables the moisture removal equipment and gas treatment equipment processes to be modified so that they are smaller, operate more efficiently, and use less power.

Until now, the heat of compression of gases, and especially landfill gases, has been either wasted to the atmosphere or only partially utilized for re-heating gases after chilling to remove moisture. This invention captures the compressor heat and coveys it to specific parts of a biogas treatment system in order to improve its efficiency and cost of operation. In addition, this invention enables the cost of the gas or vapor treatment system itself to be reduced.

In summary, the above describe system have the following benefits:

1) reduces the equipment size in comparison to other types of treatment;
2) lowers the capital cost than other technologies; and,
3) lowers the cost to operate than other technologies.

In compliance with the statute, the invention described herein has been described in language more or less specific as to structural features. It should be understood however, that the invention is not limited to the specific features shown, since the means and construction shown is comprised only of the preferred embodiments for putting the invention into effect. The invention is therefore claimed in any of its forms or modifications within the legitimate and valid scope of the amended claims, appropriately interpreted in accordance with the doctrine of equivalents.

We claim:

1. A system for utilizing the heat produce by compress gas in a biogas treatment plant, comprising:
   a. a contaminated raw bio-gas source;
   b. a first stage gas compressor connected to said raw gas source capable of compressing said raw gas;
   c. a first stage heat exchanger connected to an outside air source and to said first stage gas compressor, wherein the air from an outside air source is used to cool said compressed gas from said first stage gas compressor;
   d. an adsorber connected to said first stage heat exchanger used to strip contaminants from said cooled compressed air from said first stage heat compressor;
   e. a second stage gas compressor connected to said adsorber to receive treated gas from said adsorber;
   f. a second stage heat exchanger connected to said second stage compressor to receive compressed treated gas therefrom, said second heat exchanger being connected to said adsorber to deliver heated air thereto;
   g. a third stage compressor connected to said second stage heat exchanger to receive cooled treated gas from said second stage heat exchanger; and,
   h. a third stage heat exchanger connected to said third stage compressor, said third stage heat exchanger also being connected to an outside air source to deliver cool air thereto, said third stage heat exchanger also connected to said adsorber to deliver waste heat collected by said third stage exchanger to said adsorber.

2. The system as recited in claim 1, wherein said first stage compressor compresses the raw gas to a pressure of at least 100 psi.

3. The system as recited in claim 1, wherein said adsorber includes a canister filled with media used to remove contaminants from said cool raw gas delivered to said adsorber.

4. The system as recited in claim 3, wherein said media is made of carbon particles.

5. The system as recited in claim 1, further including a valve disposed between said inert gas generator and said adsorber to control the flow of inert gas from said inert gas generator to said adsorber.

6. The system as recited in claim 1, further including a valve disposed between said first stage heat exchanger and said adsorber to control the flow of cooled bio gas from said first stage heat exchanger and said adsorber.

7. The system, as recited in claim 1, further including a valve disposed between said first stage heat exchanger and said adsorber to control the flow of cooled bio gas from said first stage heat exchanger and said adsorber.

8. The system as recited in claim 1, further including an inert gas source connected to said absorber used to remove contaminants therefrom.

9. A system for utilizing the heat produce by compress gas in a biogas treatment plant, comprising:
   a. a contaminated bio-gas source;
   b. an adsorber connected to said bio-gas source, said absorber containing a heat exchange jacket with media located therein capable of cleaning the bio-gas delivered to said adsorber;
   c. a plurality of gas compressors each capable of compressing the bio-gas delivered thereto;
   d. a plurality of heat exchangers each connected to one said gas compressor, said heat exchanges being used to extract heat from the bio-gas compressed by said gas compressor, and;
   e. an inert gas source connected to said absorber used to remove contaminants from said media.

10. The system as recited in claim 9, further including a conduit system used to transfer the heat from one or more heat exchangers to said adsorber.

11. The system as recited in claim 9, wherein said media is made of carbon particles.

12. The system as recited in claim 9, wherein said inert gas is carbon dioxide.

13. The system as recited in claim 9, wherein said inert gas source is an on-site, inert gas generator.

14. The system as recited in claim 10, wherein said media is made of carbon particles.

15. The system as recited in claim 10, wherein said inert gas is carbon dioxide.

16. The system as recited in claim 10, wherein said insert gas source is an on-site, inert gas generator.

17. A method of recovering an adsorber filled with media used to remove contaminants in bio-gas treatment plant, comprising the following steps;
   a. selecting a system that includes an adsorber containing media used to remove contaminants from bio-gas, said adsorber connected to a bio-gas delivery conduit with at least one compressor connected thereto used to pressurize said bio-gas, said conduit being connected to a heat exchanger that removes heat from said compressed bio-gas, said system also includes an inert gas source capable of producing heated inert gas, said heated inert gas capable of removing contaminants from said media when exposed thereto, said adsorber also including an outer jacket connected to a conduit system for selectively delivering heated air from said heat exchanger;
   b. delivering contaminated bio-gas to said compressor and to said adsorber to produced clean bio-gas;
   c. determining that said media in said adsorber is spent and needs to be recycled;
   d. simultaneously activating said inert gas generator to produce inert gas that is then delivered to said adsorber and delivering said heat air from said heated exchanger to recycle said media; and,
   e. allowing said media to cool.

* * * * *